Aug. 15, 1950 L. METZGER ET AL Plant Pat. 972
APPLE TREE
Filed Oct. 17, 1947
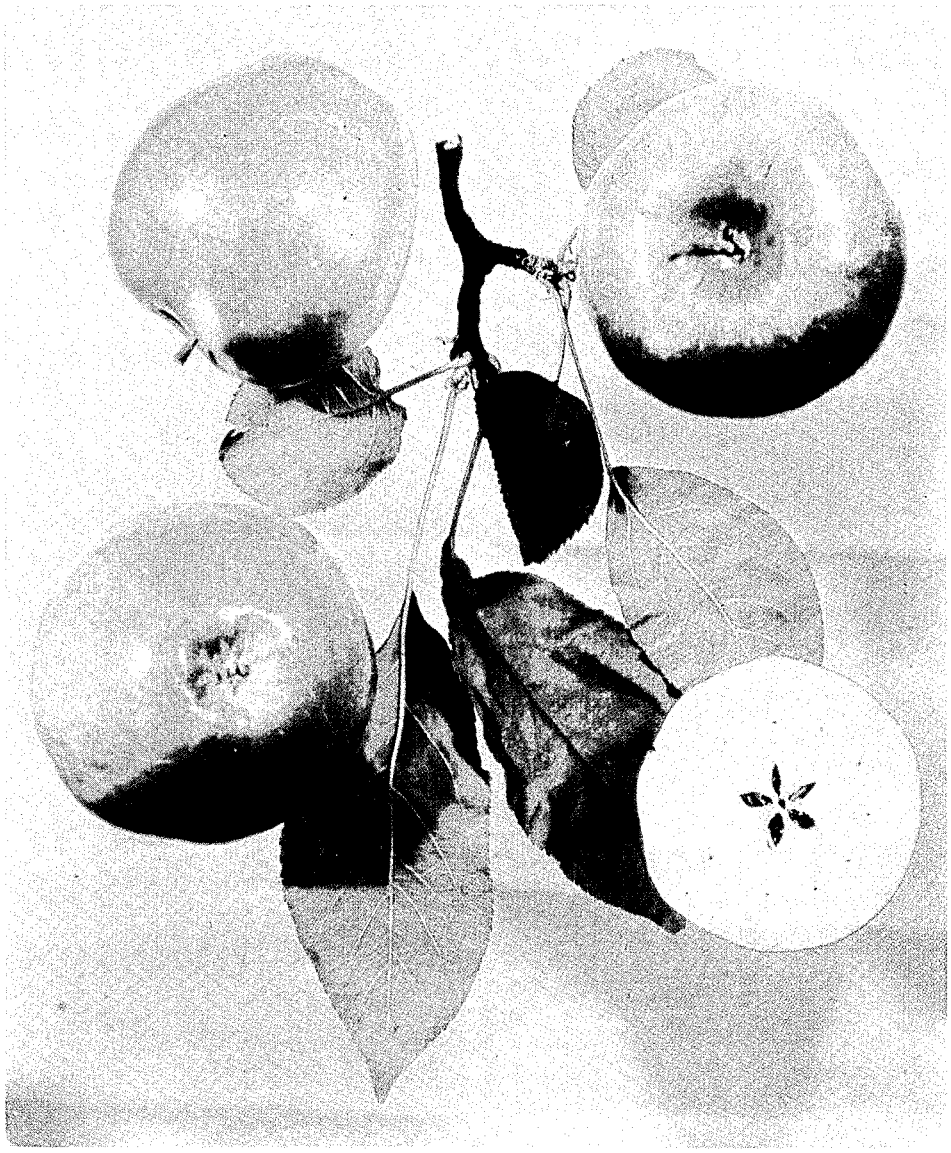
INVENTORS
LUDWIG METZGER
CECIL C CLARK
BY B M Hibbard
ATTORNEY Patented Aug. 15, 1950

Plant Pat. 972

UNITED STATES PATENT OFFICE

972

APPLE TREE

Ludwig Metzger, Seattle, and Cecil C. Clark, Wapato, Wash.

Application October 17, 1947, Serial No. 780,470

1 Claim. (Cl. 47—62)

This invention relates to a distinct and new variety of apple tree.

The drawing shows the fruit and parts of the tree of this variety.

*Description of tree*

The tree is a healthy, good sized tree, over 15 feet high with a trunk measuring about 22 inches in circumference at about 3 feet above ground. It has an open head with spreading and outward twisting branches which are slightly weeping. The branches are not easily broken. The fruit adheres well to the branches until ripe. The wood of the tree and the leaves have a yellowish color. The tree bears a heavy crop. We are inclined to believe it is a self-pollenizer.

Since the tree develops naturally a wide open head, it needs very little pruning, except for branches with a tendency to grow inward, which should be removed early. The wide open head is very advantageous for the development of the fruit and the color of the fruit, through the easy penetration of the rays from the sun.

The leaves of the tree are from three inches to five inches long, acute and finely serrated toward the outer half. Some leaves are double serrated. Smaller leaves are one inch to two inches long and more rounded.

*Description of fruit*

Size: The fruit from this apple tree averages about 3⅜″ long and has a circumference of 10″ to 13″.

Weight: 6 to 8 ounces.

Form: Oblong and conical, some ovoid.

Cavity: Starting immediately at the stem end and open gradually outward, similar to a funnel, smooth.

Basin: An average of ½″ each way with the depression side somewhat wrinkled.

Stem: From ½″ to 1″ long, green to brownish, strong and clings to apple a long time.

Skin: Smooth, thin and glossy.

Color: Red blush up to approximately 50 percent of surface, slightly striped, remainder of surface green, changing to a golden yellow, with minute dark greenish dots unevenly distributed over entire surface.

Flesh: A creamy white color.

Texture: Firm and crisp, very juicy, very good quality.

Flavor: Very agreeable, somewhat acid.

Aroma: Distinct and pleasant.

Core: Medium.

Bundle area (longitudinal): Slightly unsymmetrical with 10 dots at even distance from the core, which is characteristic of the fruit.

Seeds: 5 to 8, dark brown, depressed and pointed.

Eating quality: Excellent.

Storing and keeping: Good.

Location, fruit: The fruit described was grown at Seattle, County of King, State of Washington, and also at Wapato, County of Yakima, State of Washington.

Maturity: The fruit described ripens in Puget Sound area, State of Washington, August 20 to August 25, after Yellow Transparent and before Gravenstein. Ripens in Wapato area, County of Yakima, August 10 to August 15, after Yellow Transparent and before Jonathan and Delicious. Ripens in Yakima County, State of Washington, 10 days earlier than in King County, State of Washington.

Reproduction: The original tree from which the described fruit has been obtained was grown at Seattle, County of King, State of Washington, by the planting of a seed. The tree producing the variety of fruit described has been asexually reproduced by grafting and budding from scions taken from the original tree, and this asexual reproduction occurred at Yakima, County of Yakima, State of Washington, Wapato, County of Yakima, State of Washington, and King County, State of Washington.

What we claim is:

A new and distinct variety of apple tree substantially as shown and described, characterized by its fruit, having the characteristic configuration and color arrangements, having a texture which is firm, very juicy, and of very good quality, having a flavor which is very agreeable and somewhat acid, having an aroma which is distinct and pleasant, having eating qualities which are excellent, and having good storing and keeping properties.

LUDWIG METZGER.
CECIL C. CLARK.

No references cited.